United States Patent [19]

Hakky

[11] Patent Number: 4,890,621
[45] Date of Patent: Jan. 2, 1990

[54] CONTINUOUS GLUCOSE MONITORING AND A SYSTEM UTILIZED THEREFOR

[75] Inventor: Said I. Hakky, Largo, Fla.

[73] Assignee: Northstar Research Institute, Ltd., Philadelphia, Pa.

[21] Appl. No.: 145,066

[22] Filed: Jan. 19, 1988

[51] Int. Cl.$^4$ ............................................. A61B 5/14
[52] U.S. Cl. ..................................... 128/635; 128/637; 128/721; 604/50; 604/66
[58] Field of Search ................................. 128/632–634, 128/637, 664–667, 719, 721, 903, 635; 604/65–67, 49–53; 356/39–41

[56] References Cited

U.S. PATENT DOCUMENTS

| | | | |
|---|---|---|---|
| 3,512,517 | 5/1970 | Kadish et al. | 128/635 |
| 3,963,019 | 6/1976 | Quandt | 128/633 |
| 4,014,321 | 3/1977 | March | 128/633 |
| 4,055,175 | 10/1977 | Clemens et al. | 604/66 |
| 4,073,292 | 2/1978 | Edelman | 604/66 |
| 4,183,247 | 1/1980 | Allen et al. | 128/719 X |
| 4,206,755 | 6/1980 | Klein | 604/50 X |
| 4,403,984 | 9/1983 | Ash et al. | 604/66 X |
| 4,444,498 | 4/1984 | Heinemann | 128/633 X |
| 4,464,170 | 8/1984 | Clemens et al. | 604/50 |
| 4,484,135 | 11/1984 | Ishihara et al. | 604/66 X |
| 4,538,616 | 9/1985 | Rogoff | 604/66 X |
| 4,633,878 | 1/1987 | Bombardieri | 128/635 |
| 4,685,463 | 8/1987 | Williams | 128/632 |
| 4,774,955 | 10/1988 | Jones | 128/632 |
| 4,777,953 | 10/1988 | Ash et al. | 128/635 |

Primary Examiner—Angela D. Sykes
Attorney, Agent, or Firm—Caesar, Rivise, Bernstein, Cohen & Pokotilow, Ltd.

[57] ABSTRACT

A continuous process for monitoring blood glucose level includes the steps of segregating a clear liquid component of blood from the protein and cells of the blood, wherein the clear liquid component includes the glucose to be monitored; continuously passing the clear liquid in a predetermined path between a light-emitting and a light-detecting device; detecting an optical property of the clear liquid component of the blood and employing the optical property to determine the glucose level in the blood. The invention also relates to the system for carrying out the continuous glucose monitoring process, and to a device for automatically controlling the pressure level in the system as a function of the breathing pattern of a patient in which the system is implanted.

12 Claims, 2 Drawing Sheets

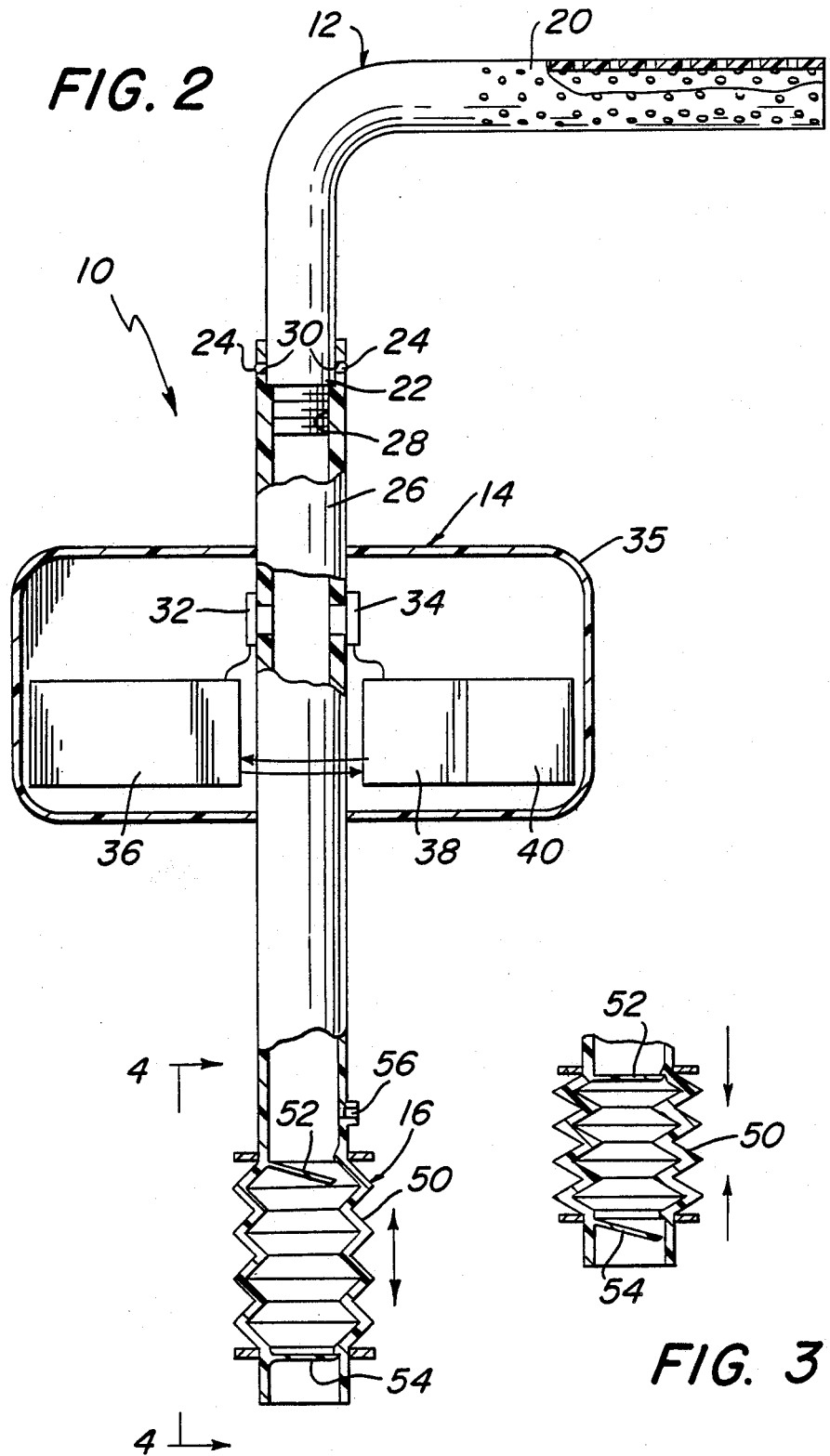

CONTINUOUS GLUCOSE MONITORING AND A SYSTEM UTILIZED THEREFOR

FIELD OF THE INVENTION

This invention relates generally to a method of continuously monitoring glucose levels in the blood, and to a system employed to carry out that method.

BACKGROUND ART

The most commonly used method for detecting and treating diabetic patients, especially type I diabetics (insulin dependent diabetes mellitus) is for the patient to provdie the hospital, doctor or laboratory technician with a specimen of urine or blood, which is then analyzed with a chemistrip to determine the level of glucose in the blood. This is not a continuous monitoring system to specifically advise a patient when it is necessary for him or her to take insulin.

A technique disclosed for the continuous monitoring of blood glucose level is disclosed in U.S. Pat. No. 4,014,321, issued to March. In accordance with the technique described in the March '321 patent polarized light is passed through the body fluids in the eye, and the optical rotation of the light, which is a measure of the glucose concentration, is then detected. The detected output is then directed by a transmitting circuit to a suitable readout device. Another patent which discloses a system for examining the body fluids in the eye to determine the blood glucose level of a patient is U.S. Pat. No. 3,963,019, issued to Quandt. The problem associated with relying upon an examination of eye fluids to determine glucose level is that such fluid is not in equilibrium with that of the blood. In fact, it may take ten (10) to twenty (20) minutes for the fluid to reach a state of equilibrium with the blood. Thus, the glucose level determined through use of the clear fluid secretions in the eye are not as reliable as are often desired.

OBJECTS OF THE INVENTION

It is a general object of this invention to provide a continuous and reliable method of monitoring blood glucose in diabetic patients.

It is a further object of this invention to employ clear body fluids in equilibrium with the blood for the purpose of reliably determining blood glucose level.

It is a further object of this invention to provide a reliable system for controlling the internal pressure in the sampling and measuring parts of the system employed for the continuous monitoring of blood glucose level.

It is a further object of this invention to provide a regulating device, operable by the normal breathing pattern of a patient, for controlling the pressure levels in the system utilized for monitoring the blood glucose level of the patient.

It is a further object of this invention to employ a telemetry arrangement as part of the blood glucose monitoring system to continuously document blood glucose levels transmitted from the measuring part of the system.

It is a more specific object of this invention to provide a blood glucose monitoring system including a sampling section for separating the glucose component of the blood from the blood cells and protein in the blood, a measuring section for measuring the glucose level separated from the blood; a regulating section for controlling the pressure in the sampling part and measuring part within desired limits and a documentation section for documenting the glucose levels determined by the measuring part of the system.

SUMMARY OF THE INVENTION

The above and other objects of this invention are achieved in a continuous method of monitoring blood glucose level including the steps of segregating a clear liquid component of blood from other components of the blood, said clear liquid component including the glucose to be measured; continuously passing said clear liquid component in a predetermined path between a light-emitting and a light-detecting system; and employing information obtained by the light-detecting system to determine the glucose level in the blood.

In accordance with the preferred method of this invention the clear liquid is separated from the protein and cells of the blood by inserting a micro-porous filter member directly into a blood vessel of the patient, wherein the clear component containing the glucose is in equilibrium with the blood. Thus, in accordance with this preferred method a reliable measure of blood glucose level is obtained.

In accordance with a preferred system of this invention a regulating member is provided for establishing a desired negative pressure level to cause the clear liquid component to be filtered from the protein and cells of the blood, and to be continuously directed past a light-emitting and light-detecting system. This regulating system preferably is controlled by the breathing activity of the patient. Specifically, in the preferred form of this invention the pressure regulating section of the system includes a bellows in fluid communication with the fluid sampling and fluid measuring parts of the system, and this bellows is connected between spaced-apart ribs of the patient, whereby the normal breathing activity of the patient causes movement of the patient's ribs, and the bellows connected thereto, to create the desired pressure conditions within the system.

Also, in accordance with the preferred embodiment of this invention the pressure regulating section of the system is valved to direct the clear liquid component of the blood, after the glucose level therein has been measured, to subcutaneous or muscle tissue in the body.

BRIEF DESCRIPTION OF THE DRAWINGS

Other objects and many of the attendant advantages of this invention will be readily appreciated as the same become better understood by reference to the following detailed description when considered in connection with the accompanying drawings wherein:

FIG. 2 is an enlarged elevational view, partly in section, illustrating the sampling, measuring and regulating sections of the glucose monitoring system;

FIG. 3 is a fragmentary sectional view of the regulating section of the glucose monitoring system illustrated in FIG. 2, but showing the arrangement of valves therein during a different portion of the patient's breathing cycle;

DESCRIPTION OF THE PREFERRED EMBODIMENT OF THE INVENTION

Figure 1:
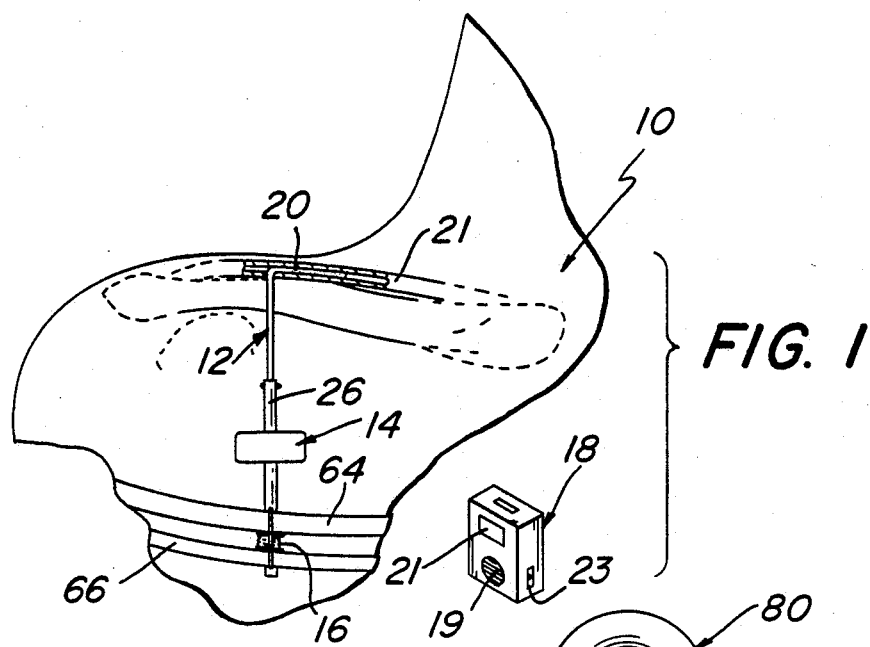
FIG. 1 is a schematic, fragmentary view illustrating a continuous glucose monitoring system in accordance with this invention, and positioned within the body of a patient for providing the glucose monitoring function.

Referring now in greater detail to the various figures of the drawings, wherein like reference characters refer to like parts, a continuous glucose monitoring system embodying the present invention is generally shown at 10 in FIG. 1. This system basically comprises a sampling section 12, wherein liquid containing the glucose to be measured is separated from the cells and protein in the blood, a measuring section 14 in which the glucose level is measured, a regulating section 16 for controlling pressure conditions within the system and for expelling the liquid back to body tissues, and a documentation section 18, which preferably is a telemetry system in the form of a receiver for receiving and storing blood glucose level information.

Referring specifically to FIGS. 1 and 2, the sampling section 12 preferably is in the form of a hollow micro-tube 20 which is inserted directly into a major blood vessel, such as the subclavian vein 21. These hollow micro-tubes 20 are well known in the medical field, and have been employed for years in hemodialysing patients with renal failure disease. In hemodialysing patients these micro-tubes are employed as a fine filter media to remove excess water, potassium chloride and sodium chloride together with creatinine and other low molecular weight materials, such as glucose.

It is important in the present invention that the hollow micro-tube 20 that is employed does not have a pore size to permit the cells or proteins in the blood to pass through it. When the hollow micro-tube 20 is inserted into the subclavian vein in accordance with this invention, a clear fluid component passes from the blood into the hollow interior of the tube, and this clear liquid component contains the moderately low molecular weight glucose as a component thereof. This clear liquid is well suited for use in determining or measuring the glucose level in the blood, as will be explained in greater detail hereinafter.

The micro-tubes 20 employed in this invention can be purchased from a number of sources, and generally has a radius of 17 to 100 angstroms, a wall thickness varying from 5 to 40 microns, an inside diameter of approximately 200 microns and a length of about 200 mm. These tubes are readily available in the market, since, as indicated above, they have been used for years in dialysis applications. For example, one well-known supplier of these materials is Organon Teknika Corporation, located in Oklahoma City, Oklahoma. The choice and selection of the required micro-tube can easily be made without any undue experimentation.

It also should be pointed out that the insertion of a micro-tube or wire into a major vein of a patient is not new, and actually has been done for years. For example, in the pacemaker art a silastic lead is inserted directly into the subclavian vein and down to the right ventricle of the heart. The other end of the lead is connected to a battery implanted under the skin of the cardiac patient. The diameter of this lead is in the range of 1-2 mm, which is greater than the diameter of the micro-tubes employed in the present invention.

As can be seen best in FIG. 2, the downstream end 22 of the micro-tube is threaded, and also is provided with projecting buttons 24 diametrically opposed to each other. This structural arrangement at the downstream end of the micro-tube is employed to connect the micro-tube into the measuring section 14 of the device. Specifically, the connection to the measuring section 14 is made through a clear, hollow silastic tube 26 having an inside diameter in the range of 250 to 300 microns. This tube includes a threaded inlet 28 and diametrically spaced-apart apertures 30 adjacent thereto, for receiving the threaded region 22 and the diametrically spaced-apart buttons 24, respectively, at the downstream end of the hollow micro-tube 20. It should be understood that other fastening means can be employed within the scope of this invention.

As can be seen best in FIG. 2, a monochromatic light source 32 and a solid-state photocell 34 are both directly embedded into the peripheral wall of the silastic tube 26, in diametrically spaced-apart locations. In this manner the photocell comes into direct contact with the clear liquid fluid of the blood directed through the silastic tube 26 from the interior of the hollow micro-tube 20. In an illustrative embodiment the solid-state photocell 34 can be of any well-known type, such as a lead sulfide cell employing a silicon diode or diode array. In the preferred embodiment the photocell includes a wavelength selector, thus accepting maximum light in the region of glucose optical activity.

Still referring to FIG. 2, the measuring section 14 of the system 10 is housed within a stainless steel casing 35, and also includes a power source 36, computer circuitry 38 and a modulator 40.

The power source 36 preferably is a long-life battery of the type employed in pacemaker systems; having a life in the range of ten to fifteen years. Suitable batteries for use in the present invention are lithium iodide batteries, lithium cupric sulfide batteries and lithium silver chromate batteries.

The computer circuit 38 is powered from the power source 36 and is connected to the photocell system to pulse the monochromatic light source 32 in the range of one to fifteen minute intervals. The precise pulse rate can be programmed on a day to day basis using the telemetry of the system. For example, the computer circuit 38 can be programmed by the telemetry to measure the blood glucose level at two minute intervals, by the computer energizing the light source 32 at such two minute intervals. The photocell 34 will then measure the optical rotation of the light, as it passes through the fluid, and the computer circuitry will calculate the concentration of glucose using the following equation:

$$C = \frac{OBS \times 100}{L \times (d) TD}$$

(d)
TD = Specific Rotation at Temp. T., with sodium-D light.
OBS = Observed rotation.
C = Gram of substance in 100 milliliter.
L = Length of the polariscope.

The computer circuit will then transmit, through the modulator 40, information representing the glucose concentration directly to the receiver 18, with the rate of transmission being at the aforementioned two minute intervals.

The computer circuit 38 is programmed to transmit an alarm signal to the receiver 18, which is located outside the body, if the blood glucose level is below a predetermined level, e.g., 70 mgm percent, or above a predetermined level, e.g., 180 mgm percent, an audible alarm, which is transmitted through speaker 19 of the receiver 18, immediately notifies the patient that his or her blood glucose level is at an abnormal or undesired level.

Referring to FIGS. 2 and 3, the regulating section 16 is of a unique construction, and is designed to maintain a negative pressure in the range of from about 10-20 mm of mercury through the hollow micro-tube 20 and the hollow silastic tube 26, to thereby provide a desired flow rate past the light source 32 and photocell 34 to permit the glucose concentration to be determined. In accordance with a preferred method of this invention the pressure conditions are set to provide an average flow rate of 0.009 cubic centimeters per minute, which is a sufficiently slow rate for an accurate measurement of the blood filtrate to be taken. It should be pointed out herein that the filtrate, being free of protein and blood cells, will not thrombose, and is a colorless clear liquid suitable for utilizing its optical properties to measure the blood glucose level thereof.

As can be seen best in FIGS. 2 and 3, the regulating section 16 includes a bellows 50 which is connected into the silastic tube 26, and is separated from the tube at upstream and downstream ends thereof by a one-way proximal valve 52 and a one-way distal valve 54, respectively. As will be explained in greater detail hereinafter, the bellows 50 actually is connected to the ribs of the patient so that the breathing function of the patient is relied upon to operate the bellows, which in conjunction with the valves 52 and 54 establishes the desired negative pressure conditions within the glucose monitoring system 10.

During inspiration by a patient the bellows 50 and valves 52 and 54 are as shown in FIG. 2, with the one-way valve 54 at the distal end of the bellows closed, thus preventing outside fluid from entering the glucose monitor. In addition this creates the desired negative pressure needed for filtration.

During expiration by a patient the bellows 50 and valves 52 and 54 are as shown in FIG. 3, with the proximal one way valve 52 closed, thus preventing the fluid in the bellows from returning to the measuring section 14 of the system. In this condition the distal valve 54 opens and expels the liquid content inside the bellows to the subcutaneous or muscular tissue. In this regard it should be noted that the whole glucose sensor system 10, except for receiver 18, is implanted under the skin.

In the preferred embodiment of this invention a pressure release valve 56 is provided adjacent the upstream end of the bellows and is designed to open in the event that the pressure within the silastic tube 26 exceeds 20 mm of mercury. It is apparent that this relief valve is important to prevent an undesired rupturing of the system, in the event that an excessive pressure build-up occurs.

During heavy exercise the amount of pressure inside the bellows 50 can reach the maximum of 20 mm of mercury, due to rapid breathing. Thus, more fluid will be filtered, should the need to measure the blood glucose at one minute intervals arise. On the other hand during sleep, respiration is slower, and the bellows 50 will be moved at a slower rate to reduce the volume of fluid being filtered per unit of time. In this latter condition the filtration pressure will be in the range of about 10 mm of mercury. It also should be noted that the fluid expelled into the muscle or subcutaneous tissue will be absorbed immediately by the body, since it contains no proteins and no blood cells.

From the above explanation it should be apparent that the regulatory section 16 provides two roles; namely, maintaining a negative pressure inside the hollow tubes of the system 10, thus assisting in filtration, and expelling the fluid passing through the measuring section 14 out of the glucose monitoring system 10, thus achieving continuous movement and measurement of blood glucose level.

Figure 4:
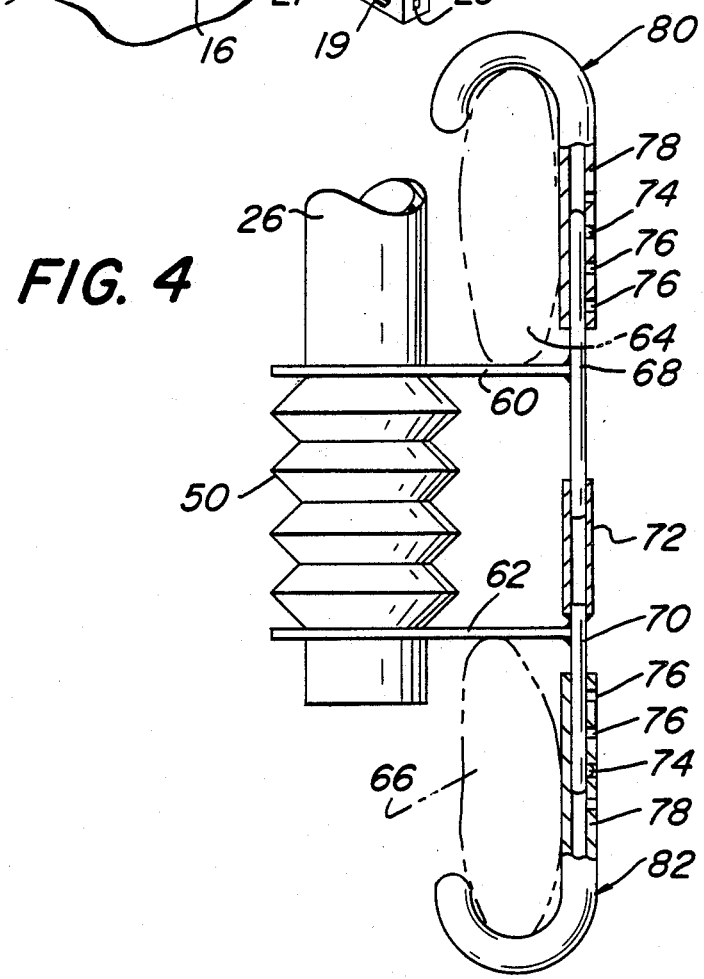
FIG. 4 is an enlarged elevational view of a part of the regulating section of the system, illustrating the arrangement for connecting the regulating system to the ribs of a patient.

Turning specifically to FIG. 4, the arrangement for connecting the bellows 50 to the ribs of a patient is illustrated. Specifically, horizontally oriented, flat members 60 and 62 are connected to opposite ends of the bellows 50 and extend between adjacent ribs 64 and 66. These members 60 and 62 are firmly attached to vertical guide rods 68 and 70, respectively, such as by welds. One end of each of the guide rods 68 and 70 is slidably received within a connecting sleeve 72 to permit relative vertical movement between the guide rods and between the plates 60 and 62 connected thereto, as a patient breathes, as will be explained in greater detail hereinafter.

Still referred to FIG. 4, the ends of the guide rods 68 and 70 remote from connecting sleeve 72 include compressible detents 74 which are receivable within complementary passages 76 extending through the side walls 78 of respective hollow hook members 80 and 82. The passages 76 preferable are spaced apart from each other at one (1) centimeter increments. The hook members 80 and 82 are vertically positioned on the guide rods 68 and 70, through the cooperation of detents 74 and complementary passages 76, so that the upper rib is closely confined between horizontal plate 60 and the upper hook section of the hook member 80, and the lower rib 66 is closely confined between the lower horizontal plate 62 and the lower hook section of the hook member 82.

In operation, as a patient inhales, thereby causing the ribs 64 and 66 to move apart, the engagement of the hook members 80 and 82 with the ribs will cause the bellows 50 to expand. Conversely, when the patient exhales, the ribs 64 and 66 will move toward each other, thereby engaging the horizontal plates 60 and 62 to compress the bellows 50. Thus, repeated breathing cycles of the patient sequentially expands and contracts the bellows 50 to aid in controlling the pressure within the glucose monitoring system 10.

Referring specifically to FIG. 1, the receiver 18 of the system 10 can be similar to any of the well-known receivers employed as part of a paging system. If desired the receiver can be adapted to be secured around a patient's belt or also can be part of a piece of jewelry, such as a bracket. The receiver can include a computer memory system for storing blood glucose levels over a 4 to 6 week period, so as to provide a continuous documentation of a patient's glucose level over that period of time.

In operation the modulator 40 of the measuring section 14 (FIG. 2) modulates the signals provided by the computer circuit 38 so that these signals can be transmitted as conventional FM signals to the receiver 18. The receiver includes a conventional tuner which can be set to receive the transmitted signal at the required frequency, and a demodulator to separate the transmitted signals representative of the glucose level from the FM carrier wave.

In accordance with this invention the diabetic patient may actually bring the receiver 18, with the glucose level information therein, to his doctor at the end of the 4 to 6 week period during which the data was stored in the receiver, or alternatively, may communicate the data directly to his attending physician via the telephone wires. In this latter case the receiver 18 also includes a suitable transmitter for modulating the stored signals and transmitting them over the telephone lines to the attending physician. This enables an attending physician to closely monitor his patient, without the need to see the patient on a frequent basis.

In the preferred embodiment of this invention the documentation section 18 includes a warning signal in the event that the blood sugar level in the patient drops below a predetermined level, e.g., 70 mgm percent, or rises above a predetermined level, e.g., 180 mgm percent. This warning signal can be in the form of a beeper signal, transmitted through the speaker 19 of the receiver 18, and also can include a read-out of the glucose level on a screen section 21 of the receiver 18.

It also is within the scope of this invention to connect the documentation section 18 directly to an insulin pump implanted within the body of the diabetic patient, and, through a control switch 23 of the documentation section 18, change the documentation section to a control member for operating the insulin pump to inject insulin into the patient, in the event that the blood sugar level of the patient drops below a predetermined minimum level.

There are many types of telemetry devices available on the market which differ very little from each other, and generally employ the same principal of operation as described herein. The choice of the desired telemetry device is well within the skill in the art, and no further elaboration is believed to be necessary herein.

Without further elaboration, the foregoing will so fully illustrate my invention that others may, by applying current or future knowledge, adopt the same for use under various conditions of service.

What is claimed as the invention is:

1. A method of continuously monitoring the glucose level in a patient including the steps of:
    establishing a negative pressure for aiding in separating a clear liquid component of the patient's blood from the blood cells and proteins thereof and for continuously passing the clear liquid component in a predetermined path by connecting a pressure regulating device to spaced-apart ribs of the patient, whereby the breathing activity of the patient is employed to establish the negative pressure;
    detecting an optical property of the clear component as it moves along said predetermined path; and
    employing information obtained regarding the detected optical property to determine the glucose level in the blood.

2. A continuous glucose monitoring system to be employed by a patient while the patient is mobile, said system including:
    microporous filter means insertable into a blood vessel of a patient for permitting a clear liquid component of the blood to filter through said filter means, said clear liquid component being separated from the blood cells and proteins of said blood and including the glucose to be monitored;
    conduit means having a passage for receiving a flow of the clear liquid component from the filter means;
    optical detecting means for detecting an optical property of the clear liquid component of the blood, said optical detecting means being adjacent the passage in the conduit means through which the clear liquid component flows;
    measuring means for determining the glucose level in the blood based on the detected optical property; and
    regulating means for controlling the flow of liquid through the passage in the conduit means and past the optical detecting means, said regulating means including a pressure regulating member and means for connecting said pressure regulating member to the ribs of a patient, whereby the breathing activity of the patient aids in regulating the pressure in the system.

3. The system of claim 2 wherein said pressure regulating member includes a bellows, and said means for connecting the bellows to the ribs includes adjustable hook means adjacent opposed ends of said bellows.

4. A device for regulating fluid flow in a system, wherein the system is adapted to be secured to an animal, said device including control means connected to the system and movable between first and second positions for aiding in controlling fluid flow through the system, and attachment means forming part of the control means and being attachable to an internal, movable part of the animal for causing the control means to move between said first and second positions as the animal breathes.

5. The device of claim 4 wherein said attachment means includes hook means attachable to spaced-apart ribs of the animal.

6. The device of claim 4 wherein said device is adapted to be inserted inside a human body and said attachment means are adapted to be attached to adjacent ribs of said human body.

7. The device of claim 4 wherein the control means includes a bellows movable between a first expanded condition and a second compressed condition.

8. The device of claim 7 wherein said attachment means includes hook means attachable to spaced-apart ribs of the animal.

9. A method of segregating a clear liquid component of a patient's blood from the blood cells and proteins of said blood including the steps of:
    a. inserting a filter member within a blood vessel of the patient and;
    b. connecting a pressure regulating device to spaced-apart ribs of the patient, whereby the breathing activity of the patient is employed to establish a pressure differential across the filter member for aiding in directing the clear liquid component of the blood through the filter member and for directing said clear liquid component out of the blood vessel to thereby separate the clear liquid component from the blood cells and proteins.

10. The method of claim 9 where the filter member is a hollow member, including the steps of filtering the clear liquid component of the blood into the hollow interior of said filter member and thereafter removing the clear liquid component from the hollow interior of said filter member to a location within the patient's body but remote from the patient's blood vessel.

11. In a glucose monitoring system to be employed by a patient while the patient is mobile, a microporous filter means insertable into a blood vessel of the patient for permitting a clear liquid component of the blood to be separated from the blood cells and proteins of the blood by being filtered through said filter means, said clear liquid component including the glucose to be monitored ; and means securable to internal, movable parts of the patient's body for establishing a pressure differential through said microporous filter means for directing the clear liquid component of the blood through said filter means.

12. The system of claim 11 wherein said microporous filter means is a hollow filter member having a continuous, microporous wall, whereby the clear liquid component of the blood is directed through said microporous wall into the hollow interior of said filter member.

* * * * *